(12) United States Patent
Mohamed et al.

(10) Patent No.: US 9,097,682 B2
(45) Date of Patent: Aug. 4, 2015

(54) OPTICAL PROBE FOR MEASURING PHYSICAL AND CHEMICAL CHARACTERISTICS OF A MEDIUM DURING FLOW

(75) Inventors: Ajmal Mohamed, Palaiseau (FR); Raphaël Vallon, Reims (FR)

(73) Assignee: ONERA (Office National d'Etudes et de Recherches Aerospatiales), Chatillon (FR)

( * ) Notice: Subject to any disclaimer, the term of this patent is extended or adjusted under 35 U.S.C. 154(b) by 218 days.

(21) Appl. No.: 13/994,055

(22) PCT Filed: Dec. 12, 2011

(86) PCT No.: PCT/FR2011/052944
§ 371 (c)(1),
(2), (4) Date: Jun. 13, 2013

(87) PCT Pub. No.: WO2012/080639
PCT Pub. Date: Jun. 21, 2012

(65) Prior Publication Data
US 2013/0258344 A1    Oct. 3, 2013

(30) Foreign Application Priority Data
Dec. 13, 2010    (FR) ...................................... 10 60411

(51) Int. Cl.
*G01N 21/00* (2006.01)
*G01N 21/85* (2006.01)

(52) U.S. Cl.
CPC ............ *G01N 21/85* (2013.01); *G01N 21/8507* (2013.01); *G01N 2021/8535* (2013.01)

(58) Field of Classification Search
CPC .................. G01N 2021/8535; G01N 21/8507; G01N 21/85
USPC .......................................... 356/410, 440, 436
See application file for complete search history.

(56) References Cited

U.S. PATENT DOCUMENTS

| | | | | |
|---|---|---|---|---|
| 4,688,943 A | * | 8/1987 | Modarress | 356/436 |
| 5,841,545 A | * | 11/1998 | Young | 356/436 |
| 6,653,611 B2 | | 11/2003 | Eckelkamp-Baker et al. | |
| 6,700,109 B2 | | 3/2004 | Eckelkamp-Baker et al. | |
| 7,339,657 B2 | * | 3/2008 | Coates | 356/73 |
| 7,675,616 B1 | * | 3/2010 | Carney et al. | 356/326 |
| 2002/0003581 A1 | | 1/2002 | Sato et al. | |
| 2009/0021588 A1 | | 1/2009 | Border et al. | |
| 2009/0147091 A1 | | 6/2009 | Myers et al. | |

OTHER PUBLICATIONS

A. Defendini, et al., "Technology Predevelopment for Active Control of Vibration and Very High Accuracy Pointing Systems", ESA 4th Spacecraft Guidance, Navigation and Control Systems Conference, 1999, 7 pages.

* cited by examiner

*Primary Examiner* — Tarifur Chowdhury
*Assistant Examiner* — Sunghee Y Gray
(74) *Attorney, Agent, or Firm* — Patterson Thuente Pedersen, P.A.

(57) ABSTRACT

An optical probe for measuring physical and chemical characteristics of a transparent fluid medium during flow comprises two fingers parallel to one another and to the flow. Each finger consists of a solid bar of transparent material, in which a light beam propagates and is reflected on an end face of the bar, said face being situated upstream in the flow. Such an optical probe may be reduced in size, and provides results which are less sensitive to disturbances of the flow that are caused by the probe itself.

10 Claims, 3 Drawing Sheets

OPTICAL PROBE FOR MEASURING PHYSICAL AND CHEMICAL CHARACTERISTICS OF A MEDIUM DURING FLOW

PRIORITY CLAIM

The present application is a National Phase entry of PCT Application No. PCT/FR2011/052944, filed Dec. 12, 2011, which claims priority from FR Application No. 10 60411 filed Dec. 13, 2010, said applications being hereby incorporated by reference herein in their entirety.

FIELD OF THE INVENTION

The invention relates to an optical probe for measuring physical and chemical characteristics of a transparent fluid medium during flow, by detection of a light beam issuing from at least one radiation source.

BACKGROUND OF THE INVENTION

An optical probe for measuring physical and chemical characteristics of a transparent fluid medium is intended to be placed within the flow, and comprises two rigid and spaced-apart fingers having respective longitudinal axes which are parallel. The probe is oriented so that these longitudinal axes of the fingers are also parallel to the velocity vector of the flow. Each finger has an upstream end within the flow, a downstream end, and a side region of optical quality for relaying the light beam between the finger and the medium.

The downstream end of the first of the two fingers is adapted to receive the light beam issuing from the source, and the downstream end of the second of the two fingers is adapted to transmit this light beam towards a detector.

In a known manner, each upstream end of the fingers has an end face which is oblique relative to the longitudinal axis, forming together with a side surface of the same finger, a projecting corner in order to split the flow. Such a shape of the finger ends which are upstream in the flow reduces the disturbances to the flow caused by the probe, thus also reducing changes to the medium which are caused by disturbances to the flow. For example, when the flow is supersonic, the upstream end of each finger causes a shock wave in the flow, which in turn causes a variation in the density of the medium. Having the upstream ends of the fingers shaped as a projecting corner reduces such disturbing effects, so that the characteristics of the medium during flow which are obtained with the probe are more representative of the state of the medium when the probe is not present.

The side regions of optical quality of the two fingers are situated so as to transmit the light beam from one to the other through the medium, in a path between the two fingers which is not orthogonal to the velocity vector of the flow. Thus the Doppler effect which affects the detection of spectroscopic absorption bands of the medium allows obtaining a measurement of the velocity of the flow.

The article entitled "Measurements of Gas Temperature and Velocity in Hypervelocity Flows Using Diode-Laser Sensors" by S. D. Wehe et al., of the American Institute of Aeronautics and Astronautics, Inc., 1998, describes such a probe and its use. In the probe described, each finger is a hollow tube which contains several optical components such as mirrors, prisms, and lenses. The light beam is propagated within the free space inside each tube, and enters or exits through the side windows constituting the finger's regions of optical quality. By construction, these windows are at a distance from the upstream end face of the corresponding finger, in each of the two fingers of the probe. It is important to note that on the finger furthest upstream, the light beam is divided into a measurement beam that is oblique relative to the axis of the fingers in order to be able to measure a Doppler effect in the flow, and a reference beam perpendicular to the axis of the finger to avoid any contribution from this effect. FIG. 1 is a cross-sectional view of such an optical probe, with the following labels:

M: medium in which the probe is placed,
V: flow velocity vector of the medium,
F: light beam,
1: finger supplying the light beam F,
$A_1$: longitudinal axis of finger 1,
11: upstream end face of finger 1,
12: side face of finger 1,
13: optical window of finger 1,
14: internal mirror of finger 1,
15: optical fiber for introducing the light beam F,
16: downstream end of finger 1,
2: finger where the light beam F is recovered;
$A_2$: longitudinal axis of finger 2,
21: upstream end face of finger 2,
22: side face of finger 2,
23: optical window of finger 2,
24: internal mirror of finger 2,
25: light detector,
26: downstream end of finger 2.

For finger 1 (respectively 2), the end face 11 (resp. 21) together with the side face 12 (resp. 22) forms a corner projecting at an acute angle which enters the flowing medium M and has the sole function of minimizing the deviation of the streamlines around the probe in comparison to the flow when the probe is not present.

A disturbance of the flow and/or of the medium M which is generated at the upstream end of each finger 1 (resp. 2) is carried to its downstream end by the flow itself. It then affects a portion P of the medium M which is increasingly large in planes perpendicular to the longitudinal axis $A_1$ (resp. $A_2$) the further away these planes are from the upstream end face 11 (resp. 21) in the direction of the downstream end 16 (resp. 26). Depending on the velocity of the flow, the disturbed portion P of the medium M can be an area of turbulence created in the flow by each finger, or a cone of a supersonic shock wave issuing from each upstream finger end. The crosshatched areas in FIG. 1 indicate these disturbed portions P of the medium M between the two fingers. Because of the distance between the upstream end 11, 21 and the optical window 13, 23 for each finger 1, 2, a significant proportion of the length of the path of the beam F between the two fingers 1 and 2 lies within these disturbed portions P of the medium M. This results in distortion of the physical and chemical characteristics obtained with the probe, in comparison to the values of these same characteristics when no probe is present.

In addition, the structure of such an optical probe has the following disadvantages, particularly due to there being multiple components:

its high price;
the difficulty of its assembly, particularly in positioning and orienting each optical component so that the light beam F follows the correct path from the fiber 15 to the mirror 14, then to the mirror 24 through the windows 13 and 23, and finally to the detector 25;
the probe is sensitive to impacts and vibrations which could cause misalignment of some of these optical components. Errors can then result when measuring the characteristics of the flow and the medium M;

the structure of a probe with multiple components does not allow reducing its dimensions, which are on the order of 10 cm (centimeters) for the length $L_1$ of finger 1 and 5 cm for the distance $D_e$ between the longitudinal axes $A_1$ and $A_2$. Due to this, the spatial resolution of measurements which can be obtained with the probe is limited. In addition, the disturbance created by the probe in the flow cannot be reduced for this reason; and lastly, the propagation of the light beam F inside each hollow finger tube can be disturbed by accidental entry of the medium M into these tubes. Such entry of the medium M into the tubes of the fingers also alters the results obtained with the optical probe for the characteristics of the flow and the medium M.

The article by the same authors, S. D. Wehe et al., entitled "Diode-Laser Sensor for Velocity Measurements in Hypervelocity Flows", AIAA Journal, Vol. 37, No. 8, concerns the same type of probe.

Lastly, document DE 10 2008 050109, which also corresponds to US 2010/0027015, discloses an optical sensor in which the two fingers ("light guides") are of the same length, so that the light beam follows a path between these two fingers which is perpendicular to the fingers themselves. Such a sensor is suitable for measurements in a transparent fluid medium which is static, but it does not allow conducting measurements based on a Doppler effect generated by a flow of the medium parallel to the fingers. The sole function of the corners projecting at an acute angle at the end of the fingers is to support the mirrors.

In addition, the probe in documents DE 10 2008 050109 and US 2010/0027015 has oblique mirrors which are arranged at the ends of the fingers and which are constructed of thin layers, specifically layers of metal. Such layers are sensitive to the corrosion and/or ablation that may be caused by certain fluid mediums in which the probes may be used. The operation of the probe then progressively deteriorates.

SUMMARY OF THE INVENTION

Under these conditions, one object of the invention is to propose an optical probe for measuring physical and chemical characteristics of a medium during flow, which does not have the above disadvantages or in which these disadvantages are reduced.

More specifically, a first object of the invention consists of proposing such a probe of a simplified structure and a reduced cost.

A second object of the invention is to propose a probe which is smaller than the existing probes.

A third object of the invention is to propose a probe which provides measurement results that are more representative of the medium during its flow when there is no probe present.

A fourth object of the invention consists of proposing a probe which allows conducting measurements based on a Doppler effect generated by a flow of the fluid medium, when the probe is oriented in the medium so as to reduce the disturbance of the flow.

A fifth object of the invention is to propose a probe in which the measurement results are less susceptible to being altered by alignment defects in optical components or defects in the fluid-tightness of the probe relative to the medium to be measured.

Lastly, a sixth object of the invention consists of proposing a probe which has little sensitivity to the chemical corrosion or ablation that may be caused by the fluid medium to be measured in which it is immersed.

The advantage of the invention is that it provides a single means, the projecting corner, for achieving these objects. This means combines an optical function and a function to minimize deviation of the streamlines around the probe in comparison to the flow when the probe is not present.

To achieve these and other objects, the invention proposes an optical probe of the type described in the introduction, in which each finger comprises a solid bar that is a single piece of a material optically transparent to the light beam. This bar extends from the downstream end to the upstream end face of the corresponding finger, and the side region of optical quality of each finger is formed by a refracting surface between the material of the bar and the medium.

In addition, for each finger, its upstream end face is of optical quality, and its side region of optical quality is situated in the projecting corner of this finger.

In this manner, during use of the optical probe, the light beam received at the downstream end of the first finger follows the following path in the optical probe:

it is propagated rectilinearly and longitudinally in the bar of the first finger, inside the material of this bar, then it is reflected on the upstream end face of the first finger inside the bar of this finger, towards the side region of optical quality of the same first finger, then it is refracted by the refracting surface of the side region of optical quality of the first finger, from the material of the bar to the medium, towards the side region of optical quality of the second finger, then it traverses the flowing medium between the first and second fingers, then it is refracted by the refracting surface of the side region of optical quality of the second finger, from the medium to the material of the bar, in the direction of the upstream end face of the same second finger, then it is reflected on the upstream end face of the second finger inside the bar of this finger, then it is propagated rectilinearly and longitudinally within the bar of the second finger, inside the material of this bar, towards the downstream end of the second finger.

Thus, in an optical probe of the invention, each finger can consist of a single part. Its structure is thus simplified and its cost reduced. Because of this simplified structure, the probe can be miniaturized, which allows conducting measurements at a smaller spatial resolution.

In addition, such a smaller probe causes less disturbance in the flow of the medium in which it is placed, so that the obtained measurement results are more representative of the medium as it would be during flow without the presence of the probe.

At the same time, the placement of each side region of optical quality close to the upstream end face of the corresponding finger minimizes the proportion of the path of the light beam between the two fingers which could lie within a portion of the flowing medium disturbed by the probe. Indeed, this placement of the side regions of optical quality ensures that any turbulence or shockwave cone generated at the upstream end of each finger only crosses a very limited portion of the path of the light beam between the two fingers.

Lastly, as each finger consists of a solid bar, no misalignment of components or unwanted entry of the medium inside the fingers can occur.

In preferred embodiments of an optical probe of the invention, it may be adapted so that the reflections of the light beam on the respective upstream end faces of the two fingers are total reflections. In this manner, a higher light intensity can be detected during measurements. The accuracy of the values obtained for the characteristics of the medium during flow is therefore greater.

In a more preferred manner, the upstream end face of each finger of the probe may consist of a dioptric interface between the material of the corresponding bar and the fluid medium in which the probe is to be immersed. This dioptric interface may be oriented so that the light beam undergoes total internal reflection on this dioptric interface, inside the material of the bar. In the context of the invention, total internal reflection is understood to mean the mode of reflection which occurs by originating from a first dielectric refractive medium to a second dielectric medium which is less refracting than the first one, and for high values for the angle of incidence such that the proportion of the energy of the incident beam transmitted to the second medium in the form of a progressive wave is zero. With such an embodiment of the upstream end faces of the fingers, their efficiency in optical reflection is not sensitive to any corrosion or ablation caused by the media in which the probe is immersed.

The invention also proposes a device for measuring at least one physical or chemical characteristic of a transparent fluid medium during flow, this (these) characteristic(s) being selected from among: a flow velocity, a temperature of the medium, a pressure of the medium, a density of the medium, and a concentration of at least one chemical compound contained in the medium, the device comprising:

an optical probe of the invention as described above;
a variable-wavelength light source assembly which is adapted to produce the light beam and is arranged to send it to the downstream end of the first finger;
a photometric detector which is arranged to measure an intensity of the light beam transmitted between the two fingers, for each wavelength of the light source assembly during operation of the measurement device; and
means for processing measurement signals produced by the detector, which are adapted to provide a value for each selected characteristic of the medium during its flow based on a spectral analysis of measurement signals.

Preferably, the light source assembly may be a variable wavelength laser, in order to obtain greater accuracy in the values for the physical and chemical characteristics which are produced by the measurement device.

Lastly, the invention proposes a method for measuring one or more of said characteristics of the medium during flow, this method comprising the following steps:

using a measurement device as proposed by the invention;
placing the optical probe in the medium, with the longitudinal axes of the fingers being parallel to the velocity vector of the flow, and orienting towards the upstream direction of the flow the finger ends having oblique end faces which, together with the respective side surfaces of the fingers, form projecting corners;
simultaneously activating the light source assembly and the detector in order to obtain respective measurement signals for the wavelengths of the light source assembly; and
controlling the processing means to obtain a value for each selected characteristic of the medium during flow, based on spectral analysis of the measurement signals.

In a particularly advantageous manner, the method of the invention allows simultaneously obtaining values for multiple characteristics of the medium during flow. Specifically, these values can be obtained from a single spectral analysis of the same measurement signals produced by the detector. Thus the flowing medium can be characterized in a particularly complete and rapid manner.

BRIEF DESCRIPTION OF THE DRAWINGS

Other features and advantages of the invention will be apparent from the following description of some non-limiting examples, with reference to the accompanying drawings in which.

For clarity sake, the dimensions of the elements represented in these figures do not correspond to the actual dimensions nor to the ratios between the actual dimensions. In addition, the same references are used in different figures to indicate identical elements or those with identical functions.

DETAILED DESCRIPTION OF THE DRAWINGS

Figure 1:
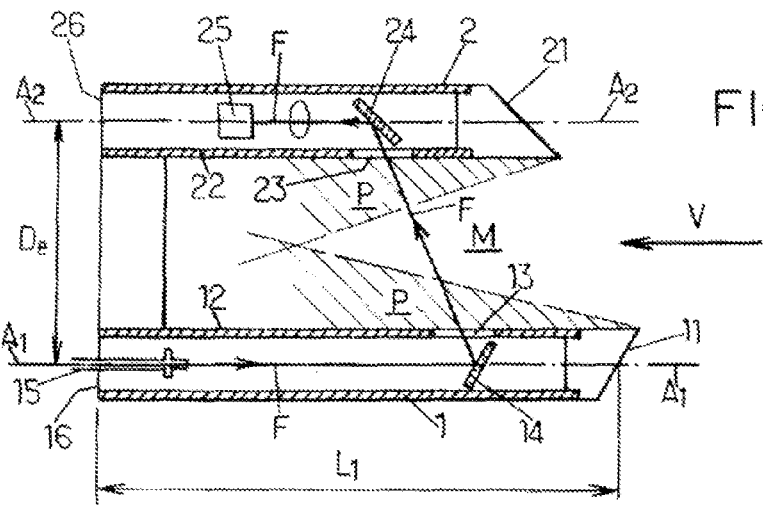
FIG. 1, already described, represents a prior art optical probe.
Figure 2:
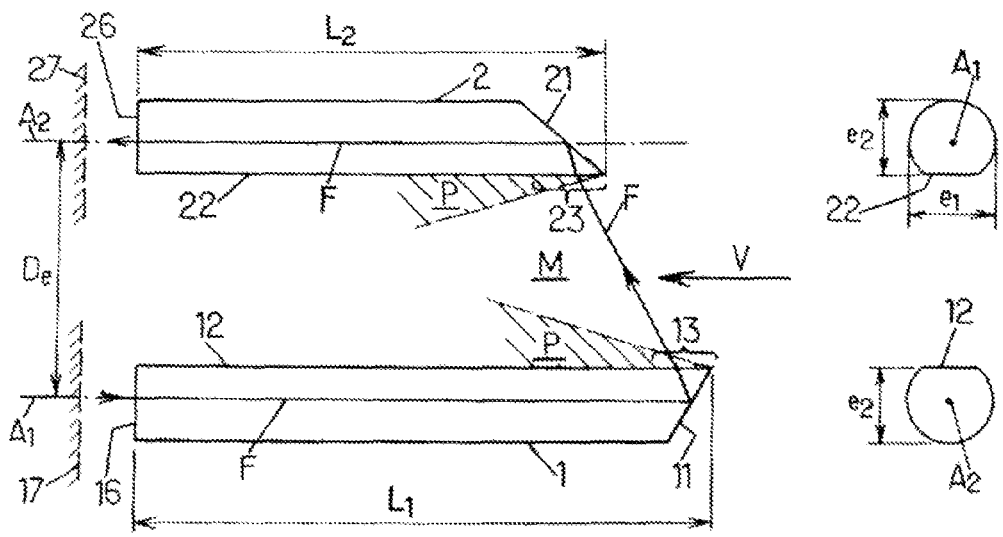
FIG. 2 represents two fingers of an optical probe of the invention, in lengthwise and transverse cross-sections.
Figure 3:
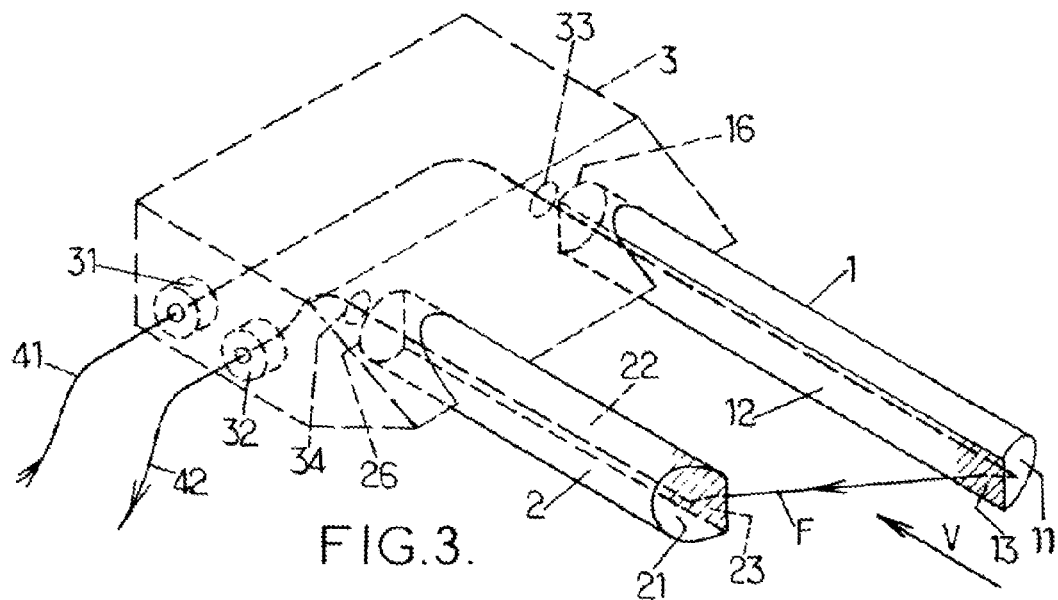
FIG. 3 is a perspective view of the fingers of FIG. 2.

FIGS. 2 and 3 show two fingers of an optical probe of the invention which each consist of a homogeneous, transparent, single-piece bar of rigid material. As in prior art FIG. 1, each finger 1 (respectively 2) has a longitudinal axis $A_1$ (resp. $A_2$), an upstream end with an end face 11 (resp. 21), a side surface, and a downstream end 16 (resp. 26). Unlike the optical probe in FIG. 1, in the invention the light beam F propagates inside the transparent material which constitutes the bar of each finger 1 and 2. The path of the beam F therefore includes longitudinally traversing the bar of finger 1, from the downstream end 16 to the upstream end face 11, with rectilinear propagation in the material of the bar of finger 1, reflecting on the face 11 which is internal to the material of the bar, exiting the bar of finger 1 by the side region 13, traversing the flowing medium M between the two fingers 1 and 2, entering the bar of finger 2 by the side region 23, reflecting internally on the face 21 of finger 2 with propagation in the material of its bar, then traversing finger 2 rectilinearly and longitudinally to its downstream end 26. The introduction of the beam F by the downstream end 16 of the finger 1 and its exit by the downstream end 26 of finger 2 will be described below.

Each bar has a sufficiently large transverse cross-section to allow the beam F to propagate within it along path segments which are each straight lines. In other words, there is no reflection of the beam F on the side surface of each bar outside the regions of optical quality.

In the invention, "region of optical quality" is understood to mean a portion of the surface of each finger which is adapted to reflect or refract the light beam F without diffusing it. In the technical terms of a person skilled in the art, these regions have been processed by optical polishing. In other words, their roughness is sufficiently low that they will not cause diffusion which would substantially reduce the intensity of the light beam along the optical path that has just been described. Preferably, this roughness may be less than half the wavelength value of the beam F, in the regions 13 and 23 and on the faces 11 and 21. Various methods for characterizing the roughness may be used here, such as X-ray reflectivity or interferometry, in particular by using a reference plate of known roughness.

In a preferred configuration of the optical probe, the side surface of each finger 1 (resp. 2) may comprise a flat face 12 (resp. 22) which contains the side region of optical quality 13 (resp. 23). For example, each bar may be obtained from a cylindrical preform having a diameter $e_1$ equal to 6 mm (millimeters), by machining a flat section along its entire length to form the flat face 12 or 22, such that the thickness $e_2$ of each bar perpendicular to the flat section is reduced to 5 mm. The machining of each bar is thus facilitated. The respective flat faces 12 and 22 of fingers 1 and 2 are then parallel to and facing one another in the optical probe.

The length $L_1$ of finger 1 may be about 70 mm, and the distance $D_e$ separating the two longitudinal axes $A_1$ and $A_2$ may be about 24 mm. In this case, the length $L_2$ of finger 2 may be about 40 mm.

The respective bars of fingers 1 and 2 are hold in position and parallel to each other by a support 3 represented with dotted lines in FIG. 3. This support 3 retains each bar by its downstream end 16 or 26, keeping them parallel to the flow of the medium M, with the upstream ends of the bars oriented in the upstream direction of the flow. Advantageously, the support 3 may also have a stream-lined shape, to reduce the disturbance it produces in the flow of the medium M as much as possible, and specifically such that such disturbance does not rise all the way to the upstream ends of the fingers 1 and 2.

In addition, the support 3 may be arranged to supply and collect the light beam F at the downstream ends of the bars of fingers 1 and 2. For example, the support 3 may comprise two optical fiber ports 31 and 32 respectively arranged to optically connect an input optical fiber 41 to the downstream end 16 of the bar of finger 1, and an output optical fiber 42 to the downstream end 26 of the bar of finger 2. The references 33 and 34 indicate components for forming the beam F which are inserted between the ends of the optical fibers 41 and 42 and the bars. Such components are known to a person skilled in the art, and may be lenses, ball lenses, or mirror collimators of small dimensions.

Alternatively, the light beam F may be supplied and collected at a distance from the downstream ends of the bars of the fingers 1 and 2. In this case, the beam F can propagate in the medium M between a light source and the support 3, as well as between the support 3 and an optical detector.

The side region of optical quality 13 (resp. 23) is on the flat face 12 (resp. 22) in immediate proximity to the upstream end face 11 (resp. 21) of the bar of finger 1 (resp. 2). As is shown in FIG. 2, this greatly reduces the proportion of the path of the beam F, between regions 13 and 23, which is contained in the portions P of the medium M disturbed by the probe itself.

The slopes of the upstream end faces 11 and 21 then have two functions. On the one hand, these faces 11 and 21 each form a projecting corner with the flat face 12 or 22 of the corresponding finger. On the other hand, they direct the reflections of the light beam F on these faces 11 and 21, inside the respective bars of fingers 1 and 2.

Figure 4:
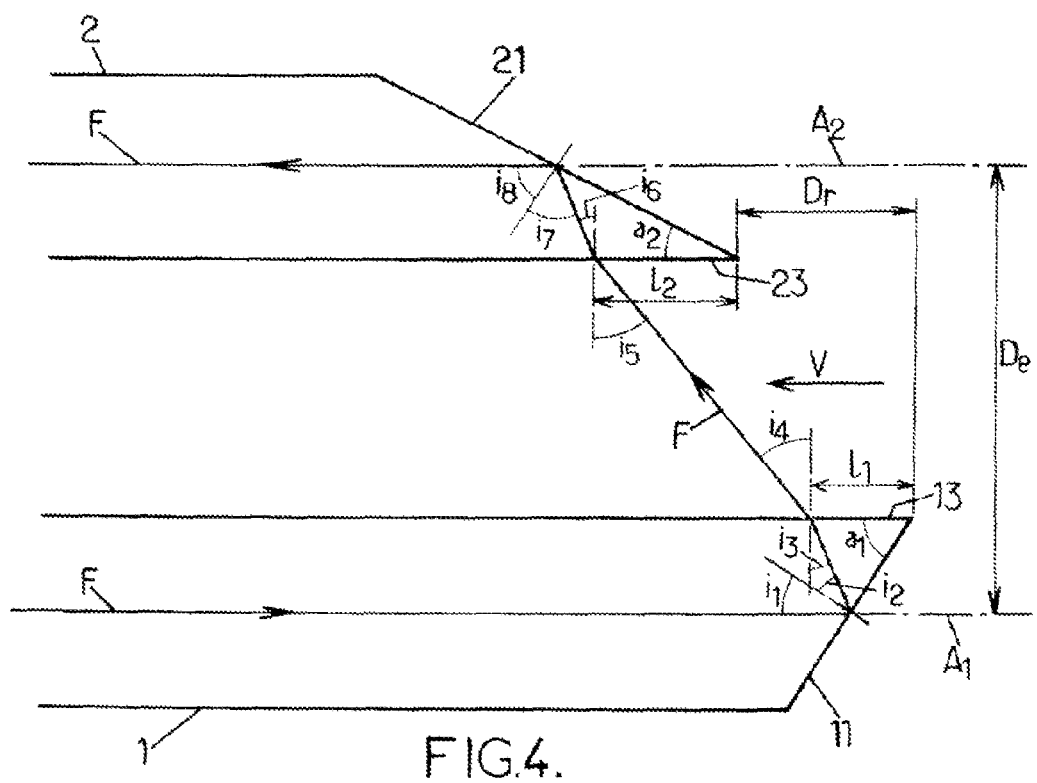
FIG. 4 is an enlargement of FIG. 2, indicating some parameters of the optical probe.

The following angles indicated in FIG. 4 are now introduced:

$i_1$: angle of incidence of the beam F on the upstream end face 11, $i_2$: angle of reflection of the beam F on the upstream end face 11, $i_3$: angle of incidence of the beam F on the side region of optical quality 13, $i_4$: angle of emergence of the beam F from the side region of optical quality 13, $i_5$: angle of incidence of the beam F on the side region of optical quality 23, $i_6$: angle of refraction of the beam F from the side region of optical quality 23, $i_7$: angle of incidence of the beam F on the upstream end face 21, $i_8$: angle of reflection of the beam F on the upstream end face 21, $a_1$: angle of the projecting corner between the upstream end face 11 and the side region of optical quality 13, and $a_2$: angle of the projecting corner between the upstream end face 21 and the side region of optical quality 23.

All these angles are calculated in relation to directions perpendicular to the surfaces of optical quality on which the reflections or refractions concerned are produced.

The Fresnel equations of reflection and refraction indicate that $i_1$ and $i_2$ are equal, $n_1 \cdot \sin i_3 = n_M \cdot \sin i_4$, $n_M \cdot \sin i_5 = n_2 \cdot \sin i_6$, and $i_7$ and $i_8$ are equal, where $n_1$, $n_2$ and $n_M$ are the respective values of the optical refractive index of the material of the bar of finger 1, the material of the bar of finger 2, and of the medium M.

Geometrically: $a_1 = 90° - i_1$, $a_1 = i_2 + i_3$, $i_4$ and $i_5$ are equal and non-zero, $a_2 = i_7 - i_6$, and $a_2 = 90° - i_8$.

In addition, the following relation leads to the distance $D_r$ the upstream end of finger 2 is offset relative to that of finger 1, as a function of the distance $D_e$ separating the longitudinal axes $A_1$ and $A_2$: $\tan i_4 = (D_r - l_2 + l_1)/D_e$, where $l_1$ (resp. $l_2$) indicates the distance between the point of the upstream end of finger 1 (resp. 2) and the point where the region 13 (resp. 23) is traversed by the light beam F.

In practice, the material of the bar of each finger 1, 2 almost always has a value for the optical refractive index for the light beam F which is greater than the value $n_M$ of the index for the medium M. For this reason, the angle $i_4 = i_5$ of the beam F between the two fingers is greater than the angles $i_3$ and $i_6$ inside each bar. To be able to determine the flow velocity from a Doppler analysis of a spectroscopic absorption band by the medium M, the angle $i_4 = i_5$ is not zero, thus ensuring that the beam F is not perpendicular to the velocity vector V between the two fingers 1 and 2. For example, the angle $i_4 = i_5$ can be taken as equal to 40° (degrees), corresponding to 50° between the beam F and the velocity vector V. Advantageously, as will be presented further below in this description, the angle $i_4 = i_5$ may alternatively be chosen to correspond to the Brewster incidence on the side regions of optical quality 13 and 23.

In the invention, it is unnecessary for the respective bars of the two fingers 1 and 2 to consist of the same transparent material. In other words, the respective materials of the two bars may be different, and a person skilled in the art will know how to choose these materials according to their refractive index values, similarly to the values of the above angles, to allow the beam F to follow the desired path.

Similarly, it is also unnecessary in the invention for the reflections of the beam F on the upstream end faces 11 and 21 to be total reflections. One will recall that a total reflection is characterized by the proportion of light energy that is reflected, this proportion being close to 100% for a reflection that is said to be total.

In order to enable reproducing the invention, two examples of optical probe structures according to the invention will now be described, in which the reflections on the upstream end faces 11 and 21 are total. However, it is understood that the various methods used in these examples to obtain the total reflections can be combined within the same probe, from one bar to the other.

In the first example, the upstream end faces 11 and 21 of fingers 1 and 2 are each equipped with a mirror which ensures that the reflections of the light beam F on these faces are total inside the corresponding bar. This mirror may comprise at least one layer of metal which is deposited on the bar, on its upstream end face. Each upstream end face mirror may also be covered with a protective layer, to prevent the mirror from being corroded by the medium M. Such upstream end face mirrors allow using, for the bars, a transparent material for which the refractive index is not particularly high. For example, bars of transparent glass of an index of about 1.5 can be used with a beam F which lies within the field of visible light, between 360 nm (nanometers) and 760 nm.

In the second example, the upstream end face 11, 21 of each of the fingers 1, 2 is a dioptric interface between the material of the corresponding bar and the medium M. The reflection of the light beam F on this upstream end face is then a total internal reflection, with an angle of incidence which is greater than a critical angle transmission value given by Snell's law. This critical angle transmission value is arcsin $(n_M/n_1)$ for finger 1, where arcsin indicates the inverse function of sine and $n_1$ is the refractive index for the material of the bar of finger 1, with an identical expression for finger 2. No layer of metal is therefore necessary at the upstream ends of the two fingers for this second example, so that such a probe is compatible with media M which may be corrosive or very hot.

However, as a function of the desired value for the angle $i_4$ of the beam F between the two fingers, the refractive index for the material of the bars must be greater than a minimum value so that the path of the beam F as proposed by the invention, inside each bar and between the two bars, is compatible with Snell's optical laws of reflection and refraction while having total internal reflections. Thus, for an $i_4$ of 40°, the refractive index for the two bars must be greater than 1.76 for the operation of the probe according to the second example to be possible.

The following Table 1 summarizes the structural parameters of such an optical probe, when the two bars consist of a neodymium-doped yttrium-aluminum garnet (YAG) having an optical refractive index which is between 1.76 and 1.85, for example equal to 1.8 for a beam F wavelength of 2.7 µm (micrometers). For these values, it has been assumed that the medium M is gaseous so that the index value $n_M$ can be considered to be equal to 1.

TABLE 1

| | |
|---|---|
| $a_1 = 55.46°$ | $a_2 = 34.54°$ |
| $i_1 = i_2 = 34.54°$ | $i_6 = 20.92°$ |
| $i_3 = 20.93°$ | $i_7 = i_8 = 55.46°$ |
| $i_4 = i_5 = 40.0°$ | $D_e = 30$ mm |

In an improvement of the invention, the optical probe may additionally comprise a first mirror 27 (FIG. 2), which is located at the downstream end of finger 2 in order to reflect the light beam F in the direction of the upstream end of the same finger 2. In this manner, the beam F traverses the medium M a second time along the same path between the two fingers 1 and 2, but in the reverse direction. This doubling of the path increases the interaction of the beam F with the medium M, so that the values obtained for the physical and chemical characteristics are more accurate. In such a configuration with a mirror 27, the beam F is both introduced into the optical probe and retrieved from it at the downstream end of finger 1. In this case, a bi-prism beam splitter (not represented) can be used to superimpose the beam to be introduced as input to the probe and the beam to be retrieved as output from it.

In such a case, where the light beam F traverses the flowing medium M in a first direction and then in a second direction that is the reverse of the first direction, it is necessary to adapt the Doppler effect analysis which is conducted in order to evaluate the velocity of the flow. In effect, each path direction corresponds to a Doppler effect which is algebraically opposite that of the other direction.

In an additional improvement, the optical probe may also comprise, in addition to the first mirror 27, a second mirror 17 which is located at the downstream end of finger 1 in order to reflect the light beam F in the direction of the upstream end of this same finger 1. In this manner, the beam F traverses the medium M multiple times along the same path between the two fingers 1 and 2, alternating between the two inverse directions of the path. The accuracy of the values obtained for the characteristics of the medium M during flow is thus further increased. In this case, at least one of the two mirrors 17 and 27 may have a residual transmission, for easily introducing and extracting the beam F in its optical path inside the optical probe. However, other methods may alternatively be used for this purpose, such as inserting a slightly reflective strip into the optical path of the beam F.

It is generally advantageous, but particularly preferred if the mirrors 17 and 27 are used, when the optical probe is designed so that the beam F passes through each refractive surface between the material of the bars and the external medium according to Brewster incidence conditions. In this manner, the beam F is transmitted across these interfaces with no loss of intensity from reflection. One should keep in mind, however, that for a dioptric interface between an incidence medium and an emergence medium of the beam F, the Brewster's angle of incidence is equal to $\arctan(n_e/n_i)$, where arctan indicates the inverse of the tangent function, $n_i$ is the refractive index value of the incidence medium, and $n_e$ is that of the emergence medium. If necessary, one can refer to general works in the field of optics for more details on Brewster incidence conditions.

Such an improvement can be applied to the introduction and/or recovery of the light beam F at the downstream ends of the two fingers 1 and 2. Thus, the downstream end 16, 26 of at least one of the two fingers 1, 2 may consist of a base surface of the corresponding bar, this base surface being oblique relative to the longitudinal axis $A_1$, $A_2$ at Brewster's angle. The light beam F is thus refracted by the base surface without reflection during use of the optical probe.

The same improvement can also be applied to the upstream ends of the fingers 1, 2, which are immersed in the medium M. The optical probe may therefore be designed so that the angle $i_4=i_5$ corresponds to Brewster incidence conditions on the refractive surfaces of the side regions of optical quality 13 and 23.

Figure 5:
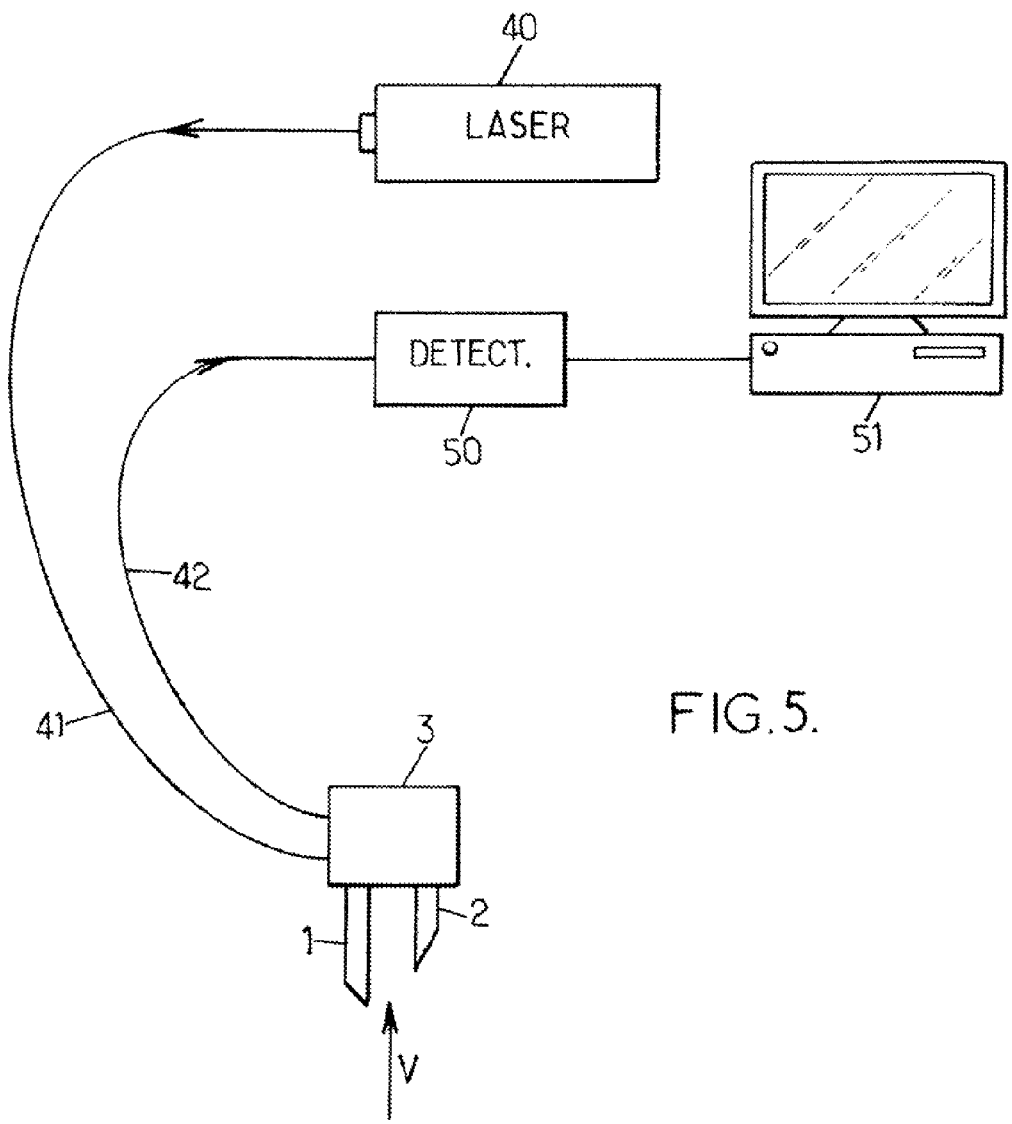
FIG. 5 illustrates a measurement device of the invention.

As shown in FIG. 5, a measurement device of the invention comprises the optical probe of FIGS. 2 to 4, a variable wavelength light source 40, a photometric detector 50, and a unit for processing measurement signals 51. Optical fiber 41 connects the source 40 to the input to the optical probe, and optical fiber 42 connects the output from the optical probe to the detector 50.

The source 40 is preferably a laser source, in order to produce the light beam F within a spectral range that is sufficiently narrow for the desired accuracy in the values for the physical and chemical characteristics of the flowing medium M. The wavelength of the source 40 is varied progressively while the optical probe is in place in the flowing medium M. This variation may be continuous or discrete depending on the type of laser source used. The variable light intensity of the beam F that is output from the optical probe is then detected in order to sample the wavelength values. The signal processing unit 51 performs a spectral analysis of the light intensity measurement signals produced by the detector 50.

Such a method for using the measurement device of the invention is similar to the one for prior art probes, and it is unnecessary to describe it further. Only the principle of the spectral analysis which is applied for some of the physical and chemical characteristics of the flowing medium M is recalled here. For a spectroscopic absorption line for a chemical compound present in the medium M:

movement of the line relative to its central wavelength when the medium M is at rest, meaning for a zero flow velocity, provides a value for the flow velocity by Doppler effect analysis;

the width of the line provides a value for the temperature of the medium M; and the area of the line provides a value for the concentration of the chemical compound in the medium M.

Such a measurement device can be used for numerous applications, including the characterization of air flows in wind-tunnel plants, or exhaust from jet nozzles or engines.

It is understood that the invention can be reproduced while introducing modifications to the embodiments described above, in order to adapt it to specific applications. In particular, the numerical values which were mentioned were only provided as examples.

The embodiments above are intended to be illustrative and not limiting. Additional embodiments may be within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

The invention claimed is:

1. An optical probe for measuring, by detection of a light beam issuing from at least one radiation source, physical and chemical characteristics of a flowing transparent fluid medium in which the probe is intended to be placed, said probe comprising two rigid fingers spaced apart from each other and having respective longitudinal axes which are parallel, the probe being intended to be oriented so that said longitudinal axes are also parallel to a flow velocity vector, each finger comprising an upstream end within the flow, a downstream end, and a side region of optical quality for transmitting the light beam between said finger and the medium, wherein the downstream end of a first one of the two fingers being adapted to receive the light beam issuing from the source, and the downstream end of a second one of the two fingers being adapted to transmit this light beam towards a detector, each upstream end of the fingers having an end face which is oblique relative to the longitudinal axis, forming together with a side surface of said finger, a projecting corner in order to split the flow, the side regions of optical quality of the two fingers being situated so as to transmit the light beam from one to the other of said regions through the medium, in a path between the two fingers which is not orthogonal to the flow velocity vector, the probe being characterized by each finger comprising a solid bar that is a single piece of a material optically transparent to the light beam, the bar extending from the downstream end to the upstream end face of said finger, and the side region of optical quality of each finger being formed by a refracting surface between the material of the bar and the medium, the upstream end face of each finger being of optical quality, and the side region of optical quality of each finger being situated in the projecting corner of said finger, and by the probe being arranged such that, during use of the probe, the light beam received at the downstream end of the first finger is propagated rectilinearly and longitudinally in the bar of the first finger, inside the material of said bar, then is reflected on the upstream end face of the first finger inside the bar of said first finger, towards the side region of optical quality of the first finger, then is refracted by the refracting surface of the side region of optical quality of the first finger, from the material of the bar of said first finger to the medium, towards the side region of optical quality of the second finger, then traverses the medium between the first and second fingers, then is refracted by the refracting surface of the side region of optical quality of the second finger, from the medium to the material of the bar of the said second finger, in the direction of the upstream end face of the second finger, then is reflected on the upstream end face of the second finger inside the bar of said second finger, then is propagated rectilinearly and longitudinally within the bar of the second finger, inside the material of said bar, towards the downstream end of the second finger, and by the probe being adapted so that the reflections of the light beam on the respective upstream end faces of the two fingers are total reflections, the upstream end face of at least one of the fingers being a dioptric interface between the material of the corresponding bar and the medium, and the reflection of the light beam on said upstream end face being a total internal reflection, with an angle of incidence of said light beam relative to a direction perpendicular to said upstream end face which is greater than a critical angle transmission value given by Snell's law.

2. The optical probe according to claim 1, wherein the material of the bar of at least one of the fingers is a neodymium-doped yttrium-aluminum garnet having an optical refractive index of between 1.76 and 1.85.

3. The optical 1 probe according to claim 1, wherein the side surface of each finger comprises a flat face, said flat face comprising the side region of optical quality of said finger, the respective flat faces of the two fingers being parallel and oriented so as to face one another.

4. The optical probe according to claim 1, additionally comprising a first mirror located at the downstream end of the second finger in order to reflect the light beam in the direction of the upstream end of said second finger, such that said light beam traverses the medium a second time along the same path between the two fingers, but in reverse direction.

5. The optical probe according to claim 4, additionally comprising a second mirror located at the downstream end of the first finger in order to reflect the light beam towards the upstream end of said first finger, such that said light beam traverses the medium multiple times along the same path between the two fingers, alternating between two inverse directions of the path.

6. The optical 1 probe according to claim 1, wherein the downstream end of at least one of the two fingers consists of a base surface of the bar, said base surface being oblique relative to the longitudinal axis of said bar at Brewster's angle, such that the light beam is refracted by said base surface without reflection during use of the optical probe.

7. A device for measuring at least one physical or chemical characteristic of a flowing transparent fluid medium, said characteristic being selected from among: a flow velocity, a temperature of the medium, a pressure of the medium, a density of the medium, and a concentration of at least one chemical compound contained in the medium, said device comprising:
- an optical probe according to claim 1;
- a variable-wavelength light source assembly, adapted to produce the light beam and arranged to send said light beam to the downstream end of the first finger;
- a photometric detector arranged to measure an intensity of the light beam transmitted between the two fingers, for each wavelength of the light source assembly during operation of said measurement device; and
- means for processing measurement signals produced by the detector, adapted to provide a value for each selected characteristic of the flowing medium based on a spectral analysis of measurement signals.

8. The device according to claim 7, wherein the light source assembly is of variable wavelength laser type.

9. A method for measuring at least one physical or chemical characteristic of a flowing transparent fluid medium, said characteristic being selected from among: a flow velocity, a temperature of the medium, a pressure of the medium, a density of the medium, and a concentration of at least one chemical compound contained in the medium, said method comprising:
- using a measurement device according to claim 7;
- placing the optical probe in the medium, with the longitudinal axes of the fingers being parallel to the flow velocity vector, and orienting towards the upstream direction of the flow the finger ends having oblique end faces which, together with the respective side surfaces of said fingers, form projecting corners;
- simultaneously activating the light source assembly and the detector in order to produce respective measurement signals for the wavelengths of the light source assembly; and
- controlling the processing means to obtain a value for each selected characteristic of the medium during flow, based on spectral analysis of the measurement signals.

10. The measurement method according to claim 9, wherein the optical probe is designed so that an angle between a direction of propagation of the light beam between the two fingers in the medium and a direction perpendicular to the side regions of optical quality, corresponds to Brewster incidence conditions for said light beam on the refractive surfaces of said side regions of optical quality of the fingers.

* * * * *